US008092773B2

(12) United States Patent
Nakanishi et al.

(10) Patent No.: US 8,092,773 B2
(45) Date of Patent: Jan. 10, 2012

(54) LIQUID FULLERENE DERIVATIVE, METHOD FOR PRODUCING THE SAME, AND DEVICE USING THE SAME

(75) Inventors: Takashi Nakanishi, Tsukuba (JP); Tsuyoshi Michinobu, Tsukuba (JP); Jonathan P. Hill, Tsukuba (JP); Katsuhiko Ariga, Tsukuba (JP)

(73) Assignee: National Institute for Materials Science, Ibaraki (JP)

( * ) Notice: Subject to any disclaimer, the term of this patent is extended or adjusted under 35 U.S.C. 154(b) by 236 days.

(21) Appl. No.: 12/309,030

(22) PCT Filed: Jul. 5, 2007

(86) PCT No.: PCT/JP2007/063502
§ 371 (c)(1),
(2), (4) Date: Jul. 13, 2009

(87) PCT Pub. No.: WO2008/004635
PCT Pub. Date: Jan. 10, 2008

(65) Prior Publication Data
US 2010/0019205 A1   Jan. 28, 2010

(30) Foreign Application Priority Data

Jul. 5, 2006 (JP) ................ 2006-185608
Apr. 2, 2007 (JP) ................ 2007-096676

(51) Int. Cl.
*C01B 31/00* (2006.01)
*H01B 1/04* (2006.01)

(52) U.S. Cl. .............. 423/445 B; 505/460; 977/734; 977/735; 252/182.1; 252/502

(58) Field of Classification Search .......... 252/182.1, 252/502; 505/460; 977/734, 735; 423/445 B
See application file for complete search history.

(56) References Cited

OTHER PUBLICATIONS

Room Temperature Liquid Fullerenes: An Uncommon Morphology of C60 Derivatives, Michinobu et al., JACS Communications, 2006, 128, 10384-10385.*
Supporting Information for Room Temperature Liquid Fullerenes: An Uncommon Morphology of C60 Derivatives, Michinobu et al., S1-S12.*
Supporting Information for Room Temperature Liquid Fullerenes: An Uncommon Morphology of C60 Derivatives, Michinobu et al., 2006, S1-S12.*

* cited by examiner

*Primary Examiner* — Mark Kopec
*Assistant Examiner* — Haidung Nguyen
(74) *Attorney, Agent, or Firm* — Wenderoth, Lind & Ponack, LLP

(57) ABSTRACT

The liquid fullerene derivative according to the present invention contains a fullerene moiety, a benzene ring bonded to the fullerene moiety, and first to third alkyl substituents $R_1$, $R_2$ and $R_3$ bonded to 2-, 4- and 6-positions of the benzene ring, respectively, and the first to third alkyl substituents $R_1$, $R_2$ and $R_3$ each contain at least 12 carbon atoms. The liquid fullerene derivative which is liquid at room temperature without requiring a solvent and easily exhibits the function of the fullerene itself, a method for producing the same, and a device using the same are provided.

9 Claims, 8 Drawing Sheets

(A)          (B)

LIQUID FULLERENE DERIVATIVE, METHOD FOR PRODUCING THE SAME, AND DEVICE USING THE SAME

TECHNICAL FIELD

The present invention relates to liquid fullerene derivatives, a method for producing the same, and a device using the same. More particularly, the invention relates to liquid fullerene derivatives which are liquid state at room temperature, a method for producing the same, and a device using the same.

BACKGROUND ART

Nanocarbons represented by fullerenes, carbon nanotubes and carbon nanohorns are expected and noted to apply to electronic materials, electrode materials, catalysts and biomaterials.

In recent years, the present inventors have developed fullerene derivatives capable of arbitrarily producing various dimensional nano-mesoscopic materials, and succeeded to construct a fullerene nanowire one-dimensionally organized on molecular level (see, for example, Patent Documents 1 and 2).

The conventionally known nanocarbons such as fullerene derivatives described in Patent Documents 1 and 2 are generally synthesized in a state that molecules are aggregated. The nanocarbons are extremely lightweight material and aggregated during stirring even though mixed with a resin, thus its handling being troublesome. Furthermore, nanocarbons are highly hydrophobic, and therefore are insoluble in polar solvents such as water, thus requiring technology for holding nanocarbons in a stably dispersed state. Moreover, nanocarbons are desirably formed into a state that even primary particles are dispersed in order to exhibit characteristics inherent in nanocarbons.

There is the technology of dispersing fullerene in water (see, for example, Patent Document 3). Patent Document 3 enables a fullerene aqueous dispersion in which fullerene is dispersed in water by using a compound having a hydrophilic group and a hydrophobic group as a dispersant of fullerene.

However, according to the technology described in Patent Document 3, it is still difficult to obtain a stabilized dispersion of high concentration in order to effectively exhibit the function of the fullerene itself.

On the other hand, synthesis of liquid (or viscous) fullerene, not dispersing fullerene in a polar solvent, is recently reported (see, for example, Non-Patent Document 1). However, fullerene described in Non-Patent Document 1 has many substituents on the fullerene core, and the function of fullerene itself is likely disturbed by such many substituents.

Patent Document 1: Japanese Patent Application No. 2005-332390
Patent Document 2: Japanese Patent Application No. 2006-125059
Patent Document 3: JP-A-2004-267972
Non-Patent Document 1: Hirsch et al., Angew. Chem. Int., Ed. 39, 1845 (2000)

DISCLOSURE OF THE INVENTION

Problems that the Invention is to Solve

Accordingly, objects of the present invention are to provide liquid fullerene derivatives which are liquid state at room temperature without requiring a solvent, and easily exhibits the function of fullerene itself, a method for producing the same, and a device using the same.

Means for Solving the Problems

The liquid fullerene derivative according to the present invention is represented by the following formula (1):

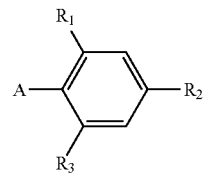

(1)

wherein $R_1$, $R_2$ and $R_3$ which are the same or different represent first to third alkyl substituents having at least 12 carbon atoms; A represents a fullerene moiety represented by the following formula (2):

(2)

wherein (Fu) represents fullerene, X represents a methyl group; and a benzene ring is bonded to a nitrogen-containing five-membered ring of the fullerene moiety A,
the first to third alkyl substituents $R_1$, $R_2$ and $R_3$ each being selected from the group consisting of alkyl ($C_nH_{2n+1}$), alkoxyl ($OC_nH_{2n+1}$) and thioalkyl ($SC_nH_{2n+1}$), wherein n is an integer of 12 or more,
and the above object is achieved by this.

The fullerene can be selected from a group consisting of $C_{60}$, $C_{70}$, $C_{76}$, $C_{84}$ and endohedral metallofullerenes.

A method for producing liquid fullerene derivatives according to the present invention is a method for producing a liquid fullerene derivative represented by the following formula (1):

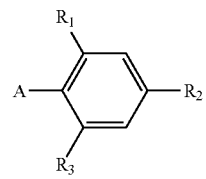

(1)

alkyl substituents having at least 12 carbon atoms; A represents a fullerene moiety represented by the following formula (2):

(2)

wherein (Fu) represents fullerene, X represents a methyl group; and a benzene ring is bonded to a nitrogen-containing five-membered ring of the fullerene moiety A, the first to third alkyl substituents $R_1$, $R_2$ and $R_3$ each being selected from the group consisting of alkyl $(C_nH_{2n+1})$, alkoxyl $(OC_nH_{2n+1})$ and thioalkyl $(SC_nH_{2n+1})$, wherein n is an integer of 12 or more, and includes a step of reacting benzaldehydes represented by the following formula (3)

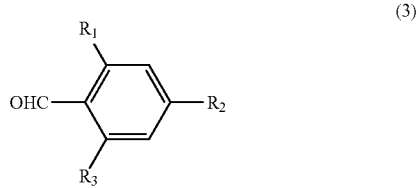

(3)

wherein $R_1$, $R_2$ and $R_3$ are the same as defined above, fullerene, and N-methylglycine, and the above object is achieved by this.

The fullerene can be selected from the group consisting of $C_{60}$, $C_{70}$, $C_{76}$, $C_{84}$ and endohedral metallofullerenes.

The reaction step can be refluxed at 110° C. for 20 to 25 hours in dried toluene.

A conductive composition according to the present invention contains the liquid fullerene derivative. Thus, the above object is achieved by this.

Electric and electronic devices according to the present invention comprise the liquid fullerene derivative as at least a part of its constitution, and the above object is achieved by this.

Advantage of the Invention

The liquid fullerene derivative according to the present invention contains alkyl substituents having 12 or more carbon atoms respectively bonded to 2-, 4- and 6-positions of a benzene ring bonded to the fullerene moiety. By virtue of this, the alkyl substituents function to weaken interaction (aggregation force) of fullerenes with each other, and therefore, the fullerene moiety can be present in a dispersed state. As a result, liquid or viscous fullerene derivatives by themselves are obtained even at room temperature.

The liquid fullerene derivative according to the present invention only contains three alkyl substituents, and therefore does not inhibit the properties of the fullerene itself. As a result, the property of the fullerene itself can effectively be exhibited. Furthermore, viscosity can be controlled by changing the number of carbon atoms present in each alkyl substituent, and as a result, fullerene derivatives having viscosity according to the intended use can be provided.

BEST MODE FOR CARRYING OUT THE INVENTION

Figure 1:
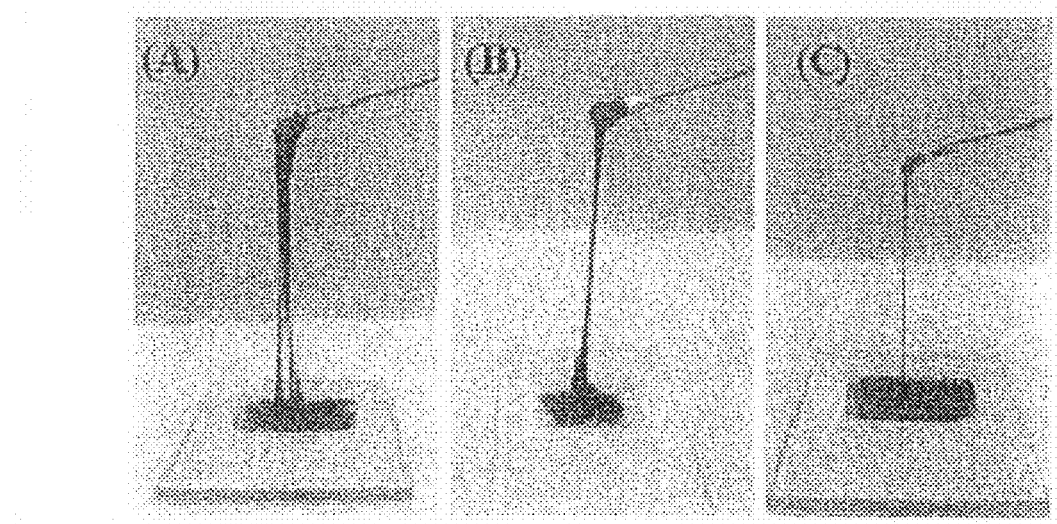
FIG. 1 is a view showing the observation result of appearance of Ex1 to Ex3 by a digital camera.

The embodiment of the present invention is described below.

The present inventors have found that, of fullerene derivatives, a fullerene derivative having a structure represented by the formula (1) is liquid by itself at least at room temperature without requiring a solvent and without having excessive substituents inhibiting the function of fullerene.

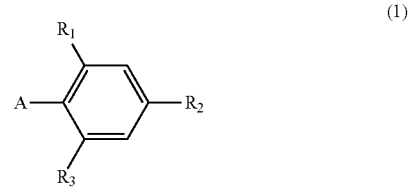

(1)

The liquid fullerene derivative according to the present invention contains a fullerene moiety (A) represented by the formula (2), a benzene ring bonded to the fullerene moiety (A), and a first alkyl substituent $R_1$, a second alkyl substituent $R_2$ and a third alkyl substituent $R_3$, bonded to 2-, 4- and 6-positions of the benzene ring, respectively. The term "alkyl substituent" used herein means an alkyl group, an alkoxy group and a thioalkyl group.

(2)

The fullerene moiety (A) represented by the formula (2) contains fullerene and a nitrogen-containing five-membered ring bonded to the fullerene, and is called fulleropyrrolidines. The fullerene is selected from the group consisting of $C_{60}$, $C_{70}$, $C_{76}$, $C_{84}$ and endohedral metallofullerenes. The endohedral metallofullerenes are a fullerene containing metal atoms in a hollow skeleton, and are represented by M@Cx. M is a metal element, and can be, for example, Sc, La, Cs and Ti. The number of metal atom contained may be one or plural. The x is a constant identifying fullerene, and can be 60, 70, 74, 80, 84 or the like. The fullerene is easily synthesized and available, and is therefore advantageous on production. The substituent X bonded to the nitrogen-containing five-membered ring is hydrogen or an alkyl group. Specific example of the alkyl group includes methyl group.

The benzene ring is bonded to the fullerene moiety (A), more specifically, the nitrogen-containing five-membered ring of the fullerene moiety (A).

The first to third alkyl substituents $R_1$ to $R_3$ are bonded to 2-, 4- and 6-positions of the benzene ring, respectively. Where alkyl substituents are bonded to positions other than the above positions of the benzene ring, the fullerene derivative obtained is not liquid at room temperature. The reason for this is that the alkyl substituents act to weaken the interaction between fullerenes by bonding the same to 2-, 4- and 6-positions. Furthermore, the fullerene derivative according to the present invention has only a substituent group on the fullerene core (i.e., one substituent group that includes the first to third alkyl substituents $R_1$ to $R_3$ at 2-, 4- and 6-position of the benzene ring). Therefore, the function of the fullerene itself is not inhibited, and the inherent characteristics such as electrochemical activity or conductivity by the fullerene can effectively be exhibited.

The first to third alkyl substituents $R_1$ to $R_3$ each contain at least 12 carbon atoms as saturated alkyl chains. When the number of carbon atoms is 12 or more, π-π interaction between fullerenes can be inhibited by the alkyl substituents, and as a result, the fullerene derivative obtained is surely liquid at room temperature. The upper limit of the number of carbon atoms is not particularly limited. However, a fullerene derivative having carbon atoms up to 22 is possible on production. The first to third alkyl substituents $R_1$ to $R_3$ may be different or the same. However, considering yield on production, cost and production time, the embodiment that the first to third alkyl substituents $R_1$ to $R_3$ are the same is preferred.

In more detail, the first to third alkyl substituents $R_1$ to $R_3$ each are selected from the group consisting of alkyl ($C_nH_{2n+1}$), alkoxyl ($OC_nH_{2n+1}$) and thioalkyl ($SC_nH_{2n+1}$), wherein n is an integer of 12 or more. When the first to third alkyl substituents $R_1$ to $R_3$ are alkyl, alkoxyl and thioalkyl, the fullerene derivative obtained can necessarily be liquid at room temperature.

The liquid fullerene derivative according to the present invention can control its viscosity by changing the number of carbon atoms in the first to third alkyl substituents $R_1$ to $R_3$. Specifically, the viscosity is increased with decreasing the number of carbon atoms, and the viscosity is decreased with increasing the number of carbon atoms. The reason for this is that the alkyl substituents inhibit π-π interaction between fullerenes by the chain length of the first to third alkyl substituents $R_1$ to $R_3$.

Thus, the liquid fullerene derivative having the desired viscosity can be obtained by controlling the number of carbon atoms in the alkyl substituents, and this is advantageous on designing a device. For example, the fullerene derivative of the present invention can be applied as a conductive filler (for example, conductive composition), utilizing conductivity of the fullerene derivative. In this case, a high viscosity fullerene derivative can be used as a conductive filler to IC, Floppy (registered trademark) disk or an electromagnetic wave shielder, and a low viscosity fullerene derivative can be used as a conductive filler to a paint or an adhesive.

The present inventors have found that the fullerene derivative having the above formula (1) is liquid at least at room temperature. In the description, the term "room temperature" means a temperature range of from 4 to 40° C., and the term "liquid" means all fullerene derivatives in a liquid state, regardless of the degree of viscosity. In more detail, the fullerene derivative according to the present invention has a decomposition temperature of 300° C. or higher, and therefore can maintain a liquid state over a wide temperature range of from room temperature to a decomposition temperature. Thus, the fullerene derivative according to the present invention can maintain a liquid state over a processing temperature range of a device, and as a result, characteristics do not change during device processing. Furthermore, the fullerene derivative according to the present invention can maintain a liquid state over a temperature range at which general devices are used, and as a result, high reliability can be secured.

A method for producing a liquid fullerene derivative according to the present invention is described below.

Step S110: 2,4,6-Substituted benzaldehydes having the first to third alkyl substituents $R_1$, $R_2$ and $R_3$ bonded to 2-, 4- and 6-positions, respectively, represented by the formula (3), fullerene and N-methylglycine are reacted. The first to third alkyl substituents $R_1$, $R_2$ and $R_3$ each contain at least 12 carbon atoms in the saturated alkyl chain mode. The upper limit of the number of carbon atoms is not particularly limited, but a substituent having up to 22 carbon atoms is possible on production, and its raw material can be available. A liquid fullerene derivative is synthesized by reacting those.

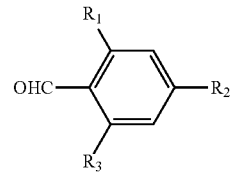

(3)

In more detail, the first to third alkyl substituents $R_1$ to $R_3$ each are selected from the group consisting of alkyl ($C_nH_{2n+1}$), alkoxyl ($OC_nH_{2n+1}$) and thioalkyl ($SC_nH_{2n+1}$), wherein n is an integer of 12 or more.

The fullerene is selected from the group consisting of $C_{60}$, $C_{70}$, $C_{76}$, $C_{84}$ and endohedral metallofullerenes. The endohedral metallofullerenes are a fullerene containing metal atoms in a hollow skeleton, and is represented by M@ Cx. M is a metal element, and can be, for example, Sc, La, Cs and Ti. The number of metal atom contained may be one or plural. The x is a constant identifying fullerene, and can be 60, 70, 74, 76, 80, 84 or the like.

The reaction is conducted at a temperature of 110° C. for from 20 to 25 hours (20 hours or more and 25 hours or less) in dried toluene while refluxing. The liquid fullerene derivative represented by the above formula (1) is obtained by this reaction. The method of the present invention proceeds under relatively mild conditions without using a special apparatus. Therefore, the liquid fullerene derivative can easily be produced and can inexpensively be produced.

In 2,4,6-substituted benzaldehydes, for example, when the first to third alkyl substituents $R_1$, $R_2$ and $R_3$ each are alkoxyl ($OC_nH_{2n+1}$), 2,4,6-trialkoxybenzaldehyde is synthesized as shown in the formula (4).

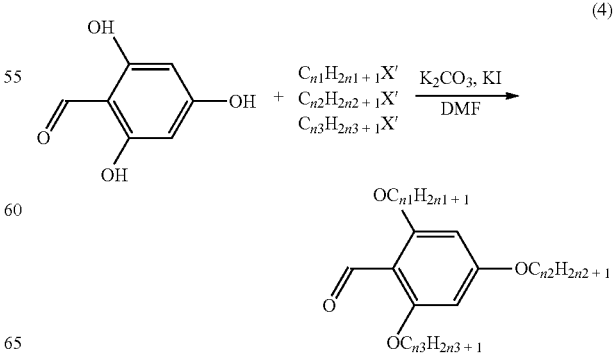

In detail, 2,4,6-trihydroxybenzaldehyde and an alkyl halide are reacted in dimethylformamide (DMF) together with potassium carbonate and potassium iodide. X' represents a halogen element such as bromine or iodine. n1, n2 and n3 each are an integer of 12 or more, and may be the same or different. However, considering yield on production, cost and production time, the embodiment that n1, n2 and n3 are the same is preferred.

Even when the first to third alkyl substituents $R_1$, $R_2$ and $R_3$ each are alkyl or thioalkyl, one skilled in the art can synthesize the aldehyde utilizing the similar scheme.

Step S120: The liquid fullerene derivative obtained in the step S110 is a crude product. Therefore, the crude product is preferably purified by conducting filtration and chromatography. A liquid fullerene derivative simple body is obtained by this.

The fullerene derivative in which the number of carbon atoms in the first to third alkyl substituents $R_1$, $R_2$ and $R_3$ each is at least 20 may again be dissolved in a volatile alkane such as hexane or heptane, and the volatile alkane may be evaporated at room temperature. By this, the fullerene derivative obtained becomes a metastable solid state at room temperature. When the fullerene derivative in a metastable solid state is once heated (for example, heated to a temperature of 55° C. or higher), its phase changes from solid to liquid. After the phase change, the fullerene derivative maintains a liquid state, and does not again change its phase to solid.

Thus, the fullerene derivative of the present invention takes a solid or liquid metastable state at room temperature, depending on the number of carbon atoms in the alkyl substituents and a solvent used in synthesis and purification. This can be advantageous in putting a device into practical use. Specifically, when the fullerene derivative according to the present invention is transported and transferred, the fullerene derivative is handled in a form of a solid, and can be liquefied on site in mounting the same on a device. Thus, handling can be simple and easy. The liquid fullerene derivative used herein can include the above-specified fullerene derivative in metastable state.

The fullerene derivative according to the present invention thus produced can be utilized in electric and electronic devices (simply referred to as a "device") such as an electrode of a secondary battery or an electrochemical capacitor. For example, when used in an electrode, the liquid fullerene derivative according to the present invention can merely be directly applied to an electrode, and this is very simple and easy as compared with the conventional method of dispersing a powder and then giving the same. Furthermore, the fullerene derivative according to the present invention is applied as an eco-friendly lead-free solder, a conductive paste and a conductive filler, utilizing high conductivity and adhesion due to the fullerene. The fullerene derivative according to the present invention can be applied to not only the above-described devices, but optional devices that can use fullerene.

Furthermore, the liquid fullerene derivative of the present invention may be used as a dispersant of a polymer. Affinity with a polymer can be improved by the substituents (that is, the first to third alkyl substituents $R_1$, $R_2$ and $R_3$ bonded to 2-, 4- and 6-positions, respectively, of the benzene ring represented by the above formula (1)) of the liquid fullerene derivative of the present invention. The liquid fullerene derivative of the present invention has extremely weak interaction of the individual derivative. As a result, the fullerene derivative can surely be dispersed in a polymer. Such a dispersed state is far excellent as compared with the conventional composite having carbon nanotubes or fullerene dispersed in a polymer. Consequently, the composite having the liquid fullerene derivative dispersed in a polymer can improve strength and abrasion resistance of a polymer as compared with the conventional composite. Examples of the dispersible polymer include polyamide, urethane, polyethylene, polyester and epoxy resin. The fullerene derivative has small surface free energy. Therefore, the presence of such a fullerene derivative on a polymer surface can add the function of improving slippage of a polymer. Thus, the liquid fullerene derivative of the present invention is preferred as a dispersant of a polymer.

The above description is given by specializing in fullerene, but a carbon nanotube derivative which is liquid at room temperature can be synthesized by changing the fullerene of the fullerene moiety (A) in the formula (1) to carbon nanotubes. The reason for this is that the organic synthesis scheme similar to the fullerene can easily be applied to the carbon nanotubes. It is known that the carbon nanotube forms a bundle structure, and as a result, aggregation force is stronger than that of the fullerene. For this reason, handling is difficult, and additionally, development of electronic function inherent in carbon nanotube is liable to be inhibited. If a liquid carbon nanotube derivative can be obtained by applying the present invention, not only the handling can be made easy, but a device effectively utilizing electronic function of carbon nanotube is expected.

The present invention is described in detail below by reference to the specific examples, but it should be understood that the invention is not limited to those examples.

EXAMPLE 1

2,4,6-Trihydroxybenzaldehyde (250 mg, 1.45 mmol), 1-bromododecane (2.15 g, 8.63 mmol), $K_2CO_3$ (600 mg, 4.34 mmol) and KI (40 mg, 0.24 mmol) were mixed in DMF (10 ml), followed by stirring at 70° C. for 20 hours. The resulting reaction product was cooled to 20° C., and chloroform (50 ml) was added thereto to separate into an organic phase and an aqueous phase. Only the organic phase was washed with salt water (100 ml) two times, and then dried using $Na_2SO_4$. The resulting crude product was purified by column chromatography (silica gel, hexane/$CH_2Cl_2$=1:1) to obtain yellow oily 2,4,6-tridecyloxybenzaldehyde (1a) (460 mg, yield: 48%). It was confirmed by $^1H$ NMR quantitative analysis that 1a is 2,4,6-tridodecyloxybenzaldehyde.

1a (300 mg, 0.455 mmol), $C_{60}$ (328 mg, 0.455 mmol) and N-methylglycine (377 mg, 4.23 mmol) were mixed in dried toluene (400 ml) in an inert gas atmosphere pressurized with dried $N_2$, followed by refluxing at 110° C. for 25 hours. The resulting reaction product was cooled to 20° C., and dried. The resulting crude product was filtered using toluene and chloroform on silica gel chromatography, and the solvents were removed under reduced pressure. The crude product from which the solvents had been removed was subjected to preparative gel permeation chromatography GPC (Bio-beads S-X3, manufactured by Bio-Rad, solvent: dried THF) to obtain a product Ex1 (319 mg, yield: 50%).

The product 1 thus obtained was a brown oily product. The product Ex1 was identified to be N-methyl-2[2,4,6-tri(dodecyl-oxy)phenyl]fulleropyrrolidine by the measurement of $^1H$ NMR (300 MHz, $CDCl_3$) and $^{13}C$ NMR (75 MHz, $CDCl_3$) by nuclear magnetic resonance apparatus (JNM-AL300, manufactured by JEOL Ltd.) and by using Fourier transform infrared spectrophotometer FT-IR (NICOLET NEXUS 670, manufactured by NICOLET, solvent: KBr), ultraviolet visible spectrophotometer UV/vis (V-570, manufactured by JASCO Corporation, solvent: hexane, using quartz cuvette), matrix assisted laser desorption ionization time-of-flight mass spectrometer MALDI-TOF-MS (Voyager-DE STR, manufactured by Applied Biosystems, matrix: HABA), and carbon-hydrogen-nitrogen simultaneous quantitative apparatus (CHN corder MT-6, manufactured by Yanaco Bunseki Kogyo Co.). The result is described hereinafter.

Appearance of the product Ex1 at 20° C. was photographed using a high resolution digital color camera (MP5Mc/OL, manufactured by Olympus Corporation). Structural analysis of the product Ex1 was conducted using powder X-ray diffraction XRD (RINT Ultima IIII, manufactured by Rigaku Corporation, accelerating voltage: 200 kV, current: 40 mV). The result is shown in FIG. 1(A) and FIG. 2(A), and is described hereinafter.

Figure 4:
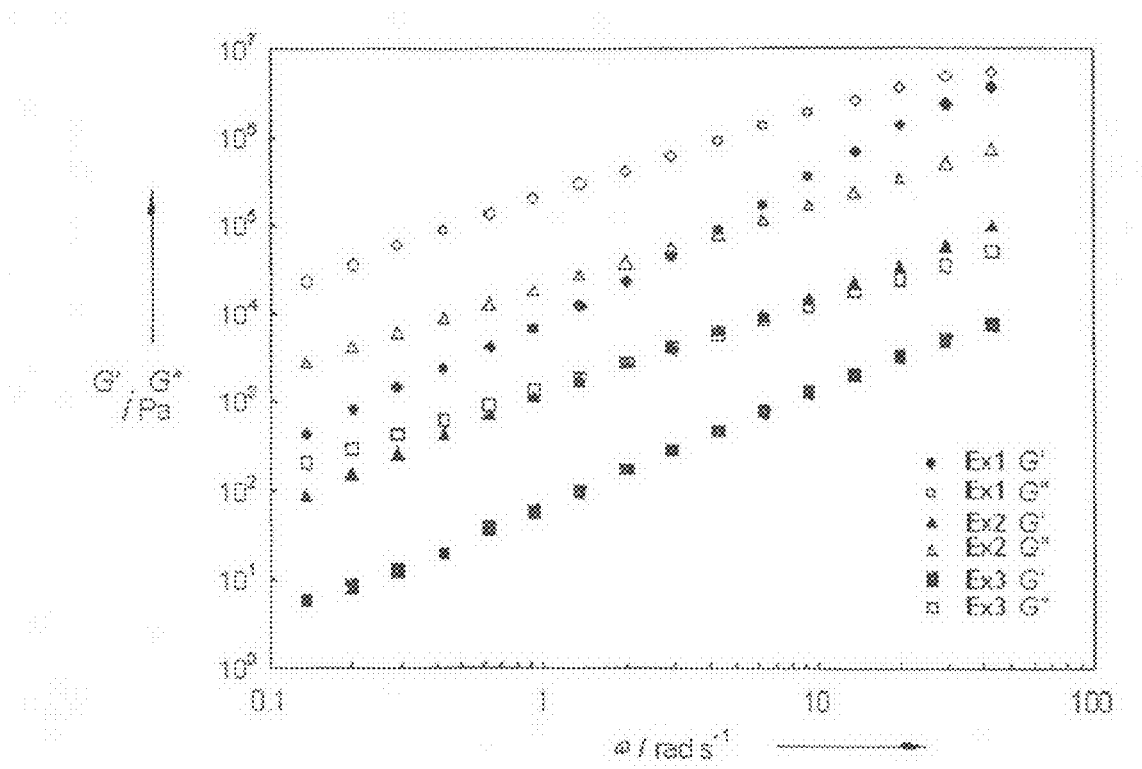
FIG. 4 is a view showing frequency dependency of storage elastic modulus G' and loss elastic modulus G" of Ex1 to Ex3.
Figure 5:
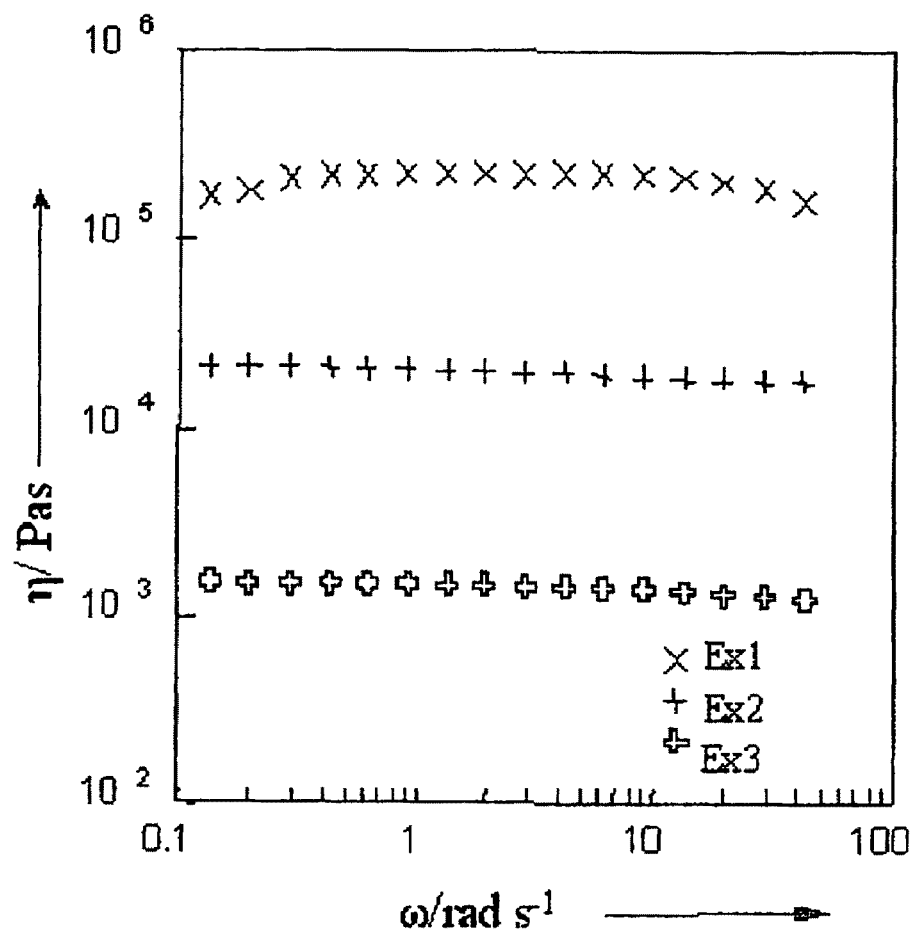
FIG. 5 is a view showing frequency dependency of viscosity of Ex1 to Ex3.

Rheologic properties of the product Ex1 were measured using rheology measurement unit (HAAKE Rheostress 1, manufactured by Thermo Electron) at 25° C. The product Ex1 was dried at 60° C. for one day in a vacuum to prepare a measuring sample. The product Ex1 was placed in a 1.0 mm thick parallel plate vessel, and frequency dependency of storage elastic modulus G' and loss elastic modulus G" was obtained. Viscosity η was calculated using Stokes-Einstein equation and Fick's law. The results are shown in FIG. 4 and FIG. 5, and are described hereinafter.

Decomposition temperature of the product Ex1 was measured using thermo gravimetry/differential thermal analyzer (EXSTAR TG/DTA6200, manufactured by Seiko Instruments Inc.). Measurement conditions were as follows. Weight change of the product Ex1 when heated to 600° C. starting from 20° C. in a heating rate of 10° C./min was measured.

Melting point of the product Ex1 was measured using differential scanning calorimeter (EXSTAR DSC6220 (with EXSTAR 6000PC Station), manufactured by Seiko Instruments Inc.). Measurement conditions were as follows. Scanning was conducted from 20° C. to −150° C., then from −150° C. to 100° C., and again from 100° C. to 20° C., and change in quantity of heat of the product Ex1 in this case was measured. Measurement results of decomposition temperature and melting point are shown in Table 1, and are described hereinafter.

Figure 8:
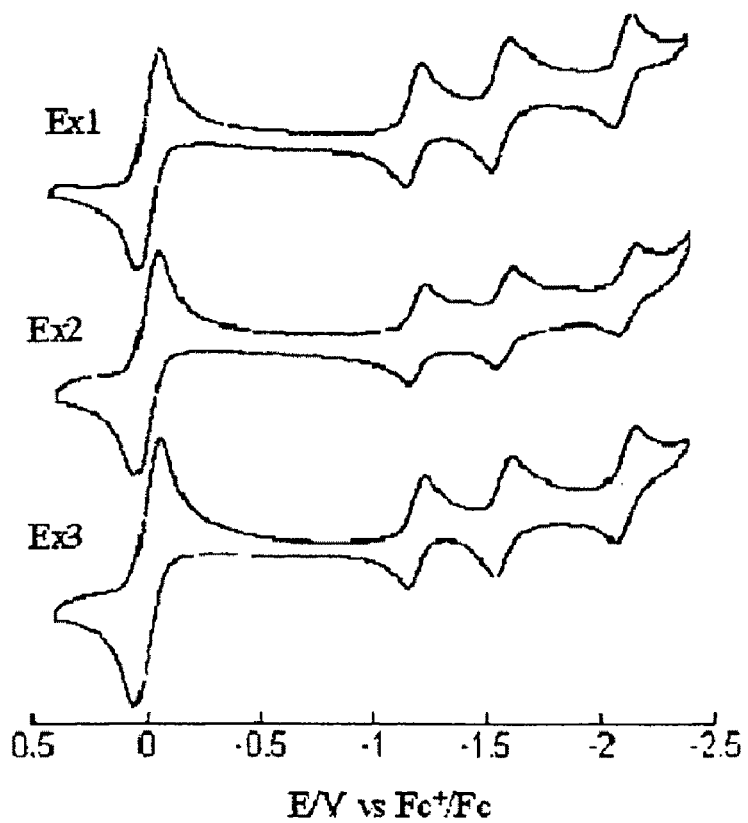
FIG. 8 is a view showing the result of cyclic voltammetric measurement of Ex1 to Ex3.

Cyclic voltammetry in the state that Ex1 was dissolved in a solvent was measured using a three electrode cell. A glassy carbon electrode (0.07 cm$^2$) was used for a working electrode, Pt was used for a counter electrode, and Ag/Ag$^+$/CH$_3$CN/nBu$_4$NClO$_4$ was used for a reference electrode. The measurement was conducted as follows. Ex1 was dissolved in CH$_2$Cl$_2$ solution containing nBu$_4$NClO$_4$ (0.1 mol), and the resulting sample was swept from 0.5V to −2.5V and from −2.5V to 0.5V in a sweeping rate of 0.1V/sec at 20° C. under Ar. The result is shown in FIG. 8, and is described hereinafter.

EXAMPLE 2

2,4,6-Trihydroxybenzaldehyde (435 mg, 2.53 mmol), 1-bromohexadecane (4.58 g, 15.0 mmol), K$_2$CO$_3$ (1.04 g, 4.52 mmol) and KI (70 mg, 0.42 mmol) were mixed in DMF (15 ml), followed by stirring at 70° C. for 20 hours. The resulting reaction product was cooled to 20° C., and chloroform (100 ml) was added thereto to separate into an organic phase and an aqueous phase. The subsequent operations are the same as in Example 1, and therefore are omitted to describe. Thus, white solid 2,4,6-trihexadecyloxybenzaldehyde (2a) was obtained (1.04 g, yield: 50%). It was confirmed by $^1$H NMR quantitative analysis that 2a is 2,4,6-trihexadecyloxybenzaldehyde.

2a (414 mg, 0.500 mmol), C$_{60}$ (360 mg, 0.500 mmol) and N-methylglycine (414 mg, 4.65 mmol) were mixed in dried toluene (450 ml), followed by refluxing at 110° C. for 25 hours. The subsequent operations are the same as in Example 1, and therefore are omitted to describe. Thus, a brown oily product Ex2 was obtained (391 mg, yield: 50%).

Similar to Example 1, it was identified using nuclear magnetic resonance apparatus and the like that the product Ex2 is N-methyl-2[2,4,6-tri(hexadecyloxy)phenyl]fulleropyrro-lidine. The result is described hereinafter.

Similar to Example 1, photography of appearance by high resolution digital color camera, structural analysis using powder X-ray diffraction XRD, measurement of frequency dependency of storage elastic modulus G' and loss elastic modulus G" using rheology measurement apparatus, and viscosity, measurement of decomposition temperature using thermo gravimetry/differential thermal analyzer, measurement of melting point using differential scanning calorimeter, and measurement of cyclic voltammetry were conducted. The results are shown in FIG. 1(B), FIG. 2(B), FIG. 4, FIG. 5, FIG. 8 and Table 1, and are described hereinafter.

EXAMPLE 3

The same operation as in Example 1 was conducted, except for using 1-bromoeicosane (3.11 g, 8.63 mmol) in place of 1-bromododecane, thereby obtaining white solid 2,4,6-trieicosyloxybenzaldehyde (3a) (445 mg, yield: 31%). It was confirmed by $^1$H NMR quantitative analysis that 3a is 2,4,6-trieicosyloxybenzaldehyde.

3a (445 mg, 0.447 mmol), C$_{60}$ (322 mg, 0.447 mmol) and N-methylglycine (370 mg, 4.15 mmol) were mixed in dried toluene (300 ml), followed by refluxing at 110° C. for 25 hours. Thereafter, the same operations as in Example 1 were conducted, and following preparative gel permeation chromatography GPC, column chromatography (silica gel, hexane/CHCl$_2$=1:2) was applied to obtain a brown oily product Ex3 (498 mg, yield: 64%).

Similar to Example 1, it was identified using nuclear magnetic resonance apparatus and the like that the product Ex3 is N-methyl-2[2,4,6-tri(eicosyloxy)phenyl]fulleropyrrolidine. The result is described hereinafter.

Similar to Example 1, photography of appearance by high resolution digital color camera, structural analysis using powder X-ray diffraction XRD, measurement of frequency dependency of storage elastic modulus G' and loss elastic modulus G" using rheology measurement apparatus, and viscosity, measurement of decomposition temperature using thermo gravimetry/differential thermal analyzer, measurement of melting point using differential scanning calorimeter, and measurement of cyclic voltammetry were conducted. The results are shown in FIG. 1(C), FIG. 2(C), FIGS. 4 to 8, FIG. 10(A) and Table 1, and are described hereinafter.

Figure 9:
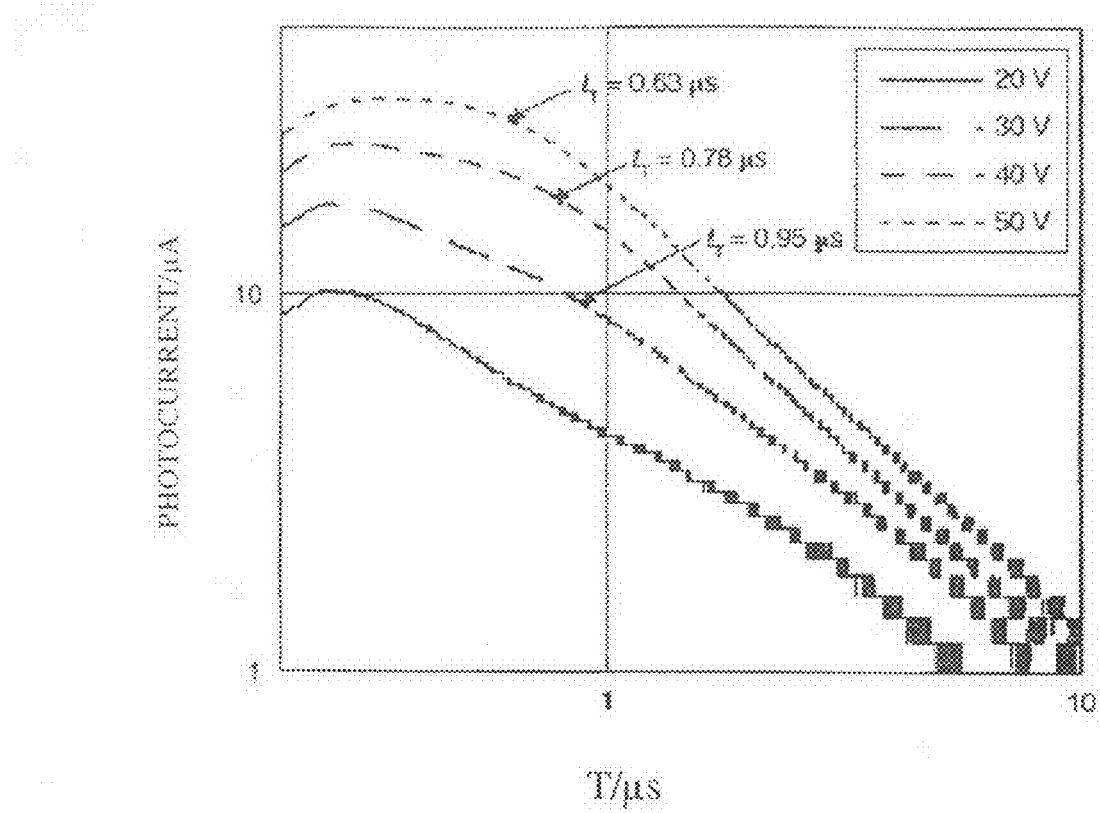
FIG. 9 is a view showing the result of transient photocurrent measurement of Ex3.

Transient photocurrent measurement by Time-Of-Flight method was conducted using digital oscilloscope. Ex3 was placed between ITO transparent electrodes to prepare a measuring sample (thickness between electrodes: 9 μm). The surface of the sample was irradiated with excitation light (pulse light) of 355 nm in the state of applying each voltage of 10V, 20V, 30V, 40V, 50V and 60V at 20° C., and current passing through the sample thereby was measured. The measurement results are shown in FIG. 9, and are described hereinafter.

Infrared absorption spectrum of Ex3 was measured using FT-IR used in Example 1. The measurement result is shown in FIG. 12(A), and is described hereinafter.

Figure 14:
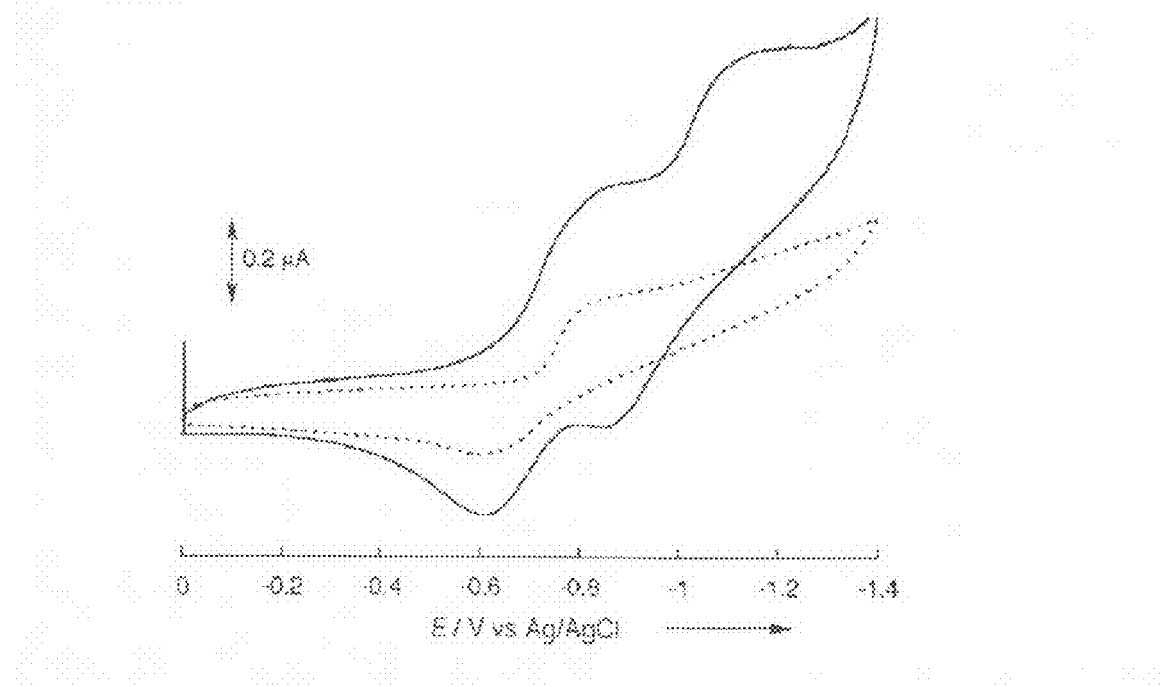
FIG. 14 is a view showing the result of cyclic voltammetric measurement of Ex3 and Ex4 applied on an electrode.

Cyclic voltammetry of a film comprising Ex3 was measured. A CH$_2$Cl$_2$ solution (5 μl, 10 mmol) containing Ex3 was deposited to a glassy carbon electrode, and dried under reduced pressure for 24 hours, thereby preparing a measuring sample. Cyclic voltammetry was measured using the glassy carbon electrode modified with Ex3 applied thereto as a working electrode, Pt counter electrode, and Ag/AgCl reference electrode. The measurement was conducted by sweeping from 0.0V to −1.4V and from −1.4V to 0.0V in a sweeping rate of 0.1V/sec at 20° C. in nBu$_4$NCl (0.1 mol) solution under Ar. The result is shown in FIG. 14, and is described hereinafter.

EXAMPLE 4

A hexane solution (10 ml, 1 mmol) containing Ex3 obtained in Example 3 was prepared. Only hexane was evaporated at 20° C. to obtain a product Ex4.

Similar to Example 1, photography of appearance by high resolution digital color camera, structural analysis using powder X-ray diffraction XRD, and measurement of glass transition point and melting point using differential scanning calorimeter were conducted, and similar to Example 3, measurement of infrared absorption spectrum by FT-IR and measurement of cyclic voltammetry were conducted. The measurement results are shown in FIG. 10(B), FIG. 11, FIG. 12(B), FIG. 13 and FIG. 14, and are described hereinafter.

COMPARATIVE EXAMPLE 1

2,4,6-Trihydroxybenzaldehyde (305 mg, 1.77 mmol), 1-bromooctane (2.03 g, 10.5 mmol), K$_2$CO$_3$ (732 mg, 530 mmol) and KI (50 mg, 0.30 mmol) were mixed in DMF (15 ml), followed by stirring at 70° C. for 24 hours. The subsequent operations are the same as in Example 1 and are therefore omitted to describe. Thus, yellow oily 2,4,6-trioctyloxy-benzaldehyde (1a') was obtained (700 mg, yield: 81%). It was confirmed by $^1$H NMR quantitative analysis that 1a' is 2,4,6-trioctyloxybenzaldehyde.

1a' (311 mg, 0.634 mmol), C$_{60}$ (456 mg, 0.633 mmol) and N-methylglycine (524 mg, 5.88 mmol) were mixed in dried toluene (400 ml), followed by refluxing at 110° C. for 20 hours. The subsequent operations are the same as in Example 3, and therefore are omitted to describe. Thus, a product Ex1' was obtained (326 mg, yield: 30%).

Similar to Example 1, it was identified using nuclear magnetic resonance apparatus and the like that the product Ex1' is N-methyl-2[2,4,6-tri(octyloxy)phenyl]fulleropyrrolidine. The result is described hereinafter.

Figure 3:
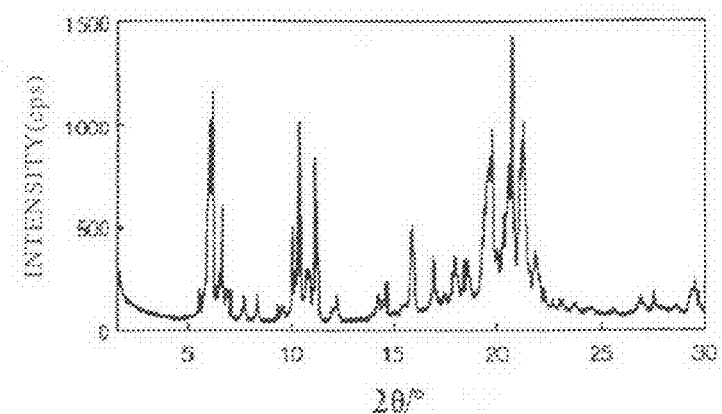
FIG. 3 is a view showing X-ray diffraction pattern of Ex1'.

Similar to Example 1, structural analysis using powder X-ray diffraction XRD, measurement of decomposition temperature using thermo gravimetry/differential thermal analyzer, and measurement of melting point using differential scanning calorimeter were conducted. The results are shown in FIG. 3 and Table 1, and are described hereinafter.

Synthetic schemes of Examples 1 to 3 and Comparative Example 1 are shown in the formula (5).

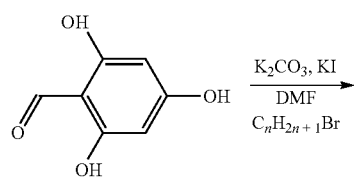

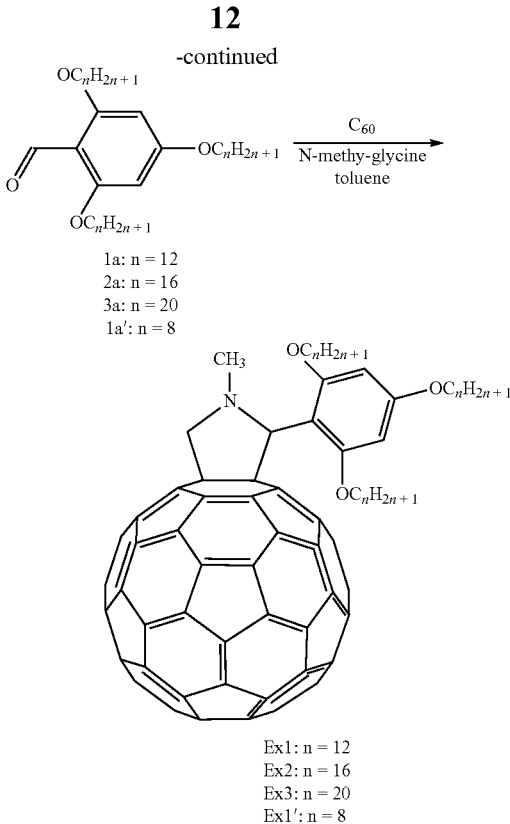

1a: n = 12
2a: n = 16
3a: n = 20
1a': n = 8

Ex1: n = 12
Ex2: n = 16
Ex3: n = 20
Ex1': n = 8

The identification results of Ex1 to Ex3 and Ex1' are shown below.

<Ex1>
$^1$H NMR (300 MHz, CDCl$_3$): δ (ppm)=0.85-0.88 (m, 9H), 1.24-2.06 (m, 60H), 2.72 (s, 3H), 3.90-3.98 (m, 6H), 4.10 (d, j=9 Hz, 1H), 4.90 (d, j=9 Hz, 1H), 5.63 (s, 1H), 6.11 (s, 2H)
$^{13}$C NMR (75 MHz, CDCl$_3$): δ (ppm)=14.09, 14.13, 22.65, 22.69, 23.91, 25.58, 26.09, 26.22, 26.26, 29.13, 29.17, 29.31, 29.34, 29.39, 29.42, 29.51, 29.55, 29.58, 29.61, 29.64, 29.67, 29.71, 29.72, 29.76, 29.83, 31.88, 31.91, 39.70, 67.67, 67.80, 67.83, 67.93, 68.65, 69.90, 69.96, 75.61, 76.70, 91.29, 91.81, 104.48, 107.92, 134.40, 135.90, 137.22, 137.26, 139.21, 139.69, 139.86, 139.89, 141.34, 141.41, 141.54, 141.79, 141.95, 142.00, 142.03, 142.07, 142.10, 142.22, 142.28, 142.38, 142.44, 142.47, 142.51, 142.94, 143.02, 144.34, 144.43, 144.58, 144.67, 144.96, 144.98, 145.01, 145.07, 145.17, 145.18, 145.24, 145.40, 145.63, 145.74, 145.78, 145.82, 145.89, 145.93, 145.95, 145.99, 146.07, 146.09, 146.22, 146.70, 146.79, 147.12, 147.22, 147.28, 154.96, 155.18, 156.21, 157.55, 159.96, 159.99, 160.62
IR (KBr): ν (cm$^{-1}$)=2922, 2851, 2766, 1605, 1585, 1463, 1440, 1377, 1329, 1217, 1165, 1113, 811
UV/vis (hexane): λ (nm) (ε)=212 (182600), 255 (119800), 311 (43100)
MALDI-TOF-MS (HABA): m/z=1405.64 [MH]$^+$ (theoretical value of C$_{105}$H$_{83}$NO$_3^+$: 1405.64)
Elemental analysis (%): C, 89.58; H, 6.00; N, 1.00 (theoretical value of C$_{105}$H$_{83}$NO$_3$: C, 89.65; H, 5.96; N, 1.00)
<Ex2>
$^1$H NMR (300 MHz, CDCl$_3$): δ (ppm)=0.85-0.89 (m, 9H), 1.23-2.00 (m, 84H), 2.71 (s, 3H), 3.90-3.98 (m, 6H), 4.09 (d, j=9 Hz, 1H), 4.88 (d, j=9 Hz, 1H), 5.62 (s, 1H), 6.10 (s, 2H)
$^{13}$C NMR (75 MHz, CDCl$_3$): δ (ppm)=14.15, 22.69, 25.60, 26.12, 26.24, 26.29, 29.20, 29.38, 29.45, 29.53, 29.61, 29.69, 29.75, 29.85, 31.93, 39.69, 67.79, 67.91, 68.64, 69.96, 75.61, 76.71, 91.30, 91.81, 104.49, 134.40, 135.90, 137.21, 137.24, 139.21, 139.68, 139.86, 139.89, 141.34, 141.39, 141.52, 141.77, 141.94, 141.99, 142.01, 142.05, 142.08, 142.22, 142.26, 142.37, 142.41, 142.46, 142.50, 142.93, 143.01, 144.33, 144.43, 144.57, 144.66, 144.94, 145.00, 145.05, 145.17, 145.24, 145.39, 145.60, 145.73, 145.77, 145.81, 145.87, 145.93, 145.98, 146.05, 146.09, 146.21, 146.70, 146.77, 147.11, 147.21, 147.26, 154.92, 155.19, 156.21, 157.56, 159.97, 160.64

IR (KBr): ν (cm$^{-1}$)=2922, 2851, 2766, 1606, 1584, 1464, 1437, 1377, 1329, 1260, 1217, 1166, 1114, 1033, 810

UV/vis (hexane): λ (nm) (ε)=212 (177300), 255 (112000), 316 (39200)

MALDI-TOF-MS (HABA): m/z=1573.45 [MH]$^+$ (theoretical value of $C_{117}H_{103}NO_3^+$: 1573.83)

Elemental analysis (%): C, 88.95; H, 6.83; N, 0.99 (theoretical value of $C_{117}H_{107}NO_3$: C, 89.22; H, 6.85; N, 0.89)

<Ex3>

$^1$H NMR (300 MHz, CDCl$_3$): δ (ppm)=0.78-0.83 (m, 9H), 1.16-1.90 (m, 108H), 2.65 (s, 3H), 3.82-3.91 (m, 6H), 4.02 (d, j=9 Hz, 1H), 4.82 (d, j=9 Hz, 1H), 5.55 (s, 1H), 6.04 (s, 2H)

$^{13}$C NMR (75 MHz, CDCl$_3$): δ (ppm)=14.13, 14.16, 22.70, 22.72, 25.60, 26.14, 26.26, 26.31, 29.22, 29.38, 29.40, 29.48, 29.55, 29.60, 29.64, 29.68, 29.73, 29.78, 29.88, 31.93, 31.95, 39.70, 67.80, 67.92, 68.65, 69.94, 69.98, 75.62, 76.74, 77.21, 91.30, 91.80, 104.49, 134.42, 135.92, 137.22, 137.26, 139.22, 139.70, 139.88, 139.91, 141.35, 141.40, 141.54, 141.79, 141.96, 142.00, 142.03, 142.07, 142.10, 142.24, 142.28, 142.39, 142.43, 142.48, 142.51, 142.95, 143.03, 144.34, 144.44, 144.59, 144.68, 144.96, 145.00, 145.02, 145.08, 145.17, 145.26, 145.41, 145.62, 145.74, 145.78, 145.83, 145.89, 145.93, 145.95, 146.00, 146.07, 146.11, 146.23, 146.72, 146.78, 147.13, 147.22, 147.28, 154.94, 155.20, 156.22, 157.58, 159.99, 160.65

IR (KBr): ν (cm$^{-1}$)=2922, 2851, 2768, 1606, 1464, 1377, 1329, 1218, 1166, 1115, 811, 721

UV/vis (hexane): λ (nm) (ε)=212 (184600), 255 (1225000), 316 (43800)

MALDI-TOF-MS (HABA): m/z=1742.02 [MH]$^+$ (theoretical value of $C_{129}H_{191}NO_3^+$: 1742.01)

Elemental analysis (%): C, 87.81; H, 7.79; N, 0.86 (theoretical value of $C_{129}H_{131}NO_3$: C, 88.87; H, 7.57; N, 0.80)

<Ex1'>

$^1$H NMR (300 MHz, CDCl$_3$): δ (ppm)=0.87-0.88 (m, 9H), 1.26-2.00 (m, 36H), 2.72 (s, 3H), 3.88-3.99 (m, 6H), 4.10 (d, j=9 Hz, 1H), 4.89 (d, j=9 Hz, 1H), 5.62 (s, 1H), 6.12 (s, 2H)

$^{13}$C NMR (75 MHz, CDCl$_3$): δ (ppm)=14.09, 14.17, 22.64, 22.71, 22.74, 26.11, 26.23, 26.29, 29.21, 29.33, 29.36, 29.39, 29.47, 29.49, 29.54, 29.62, 29.69, 31.79, 31.91, 39.70, 67.82, 67.87, 68.68, 69.93, 69.99, 75.63, 76.75, 91.35, 91.87, 104.57, 134.42, 135.93, 137.23, 137.27, 139.24, 139.72, 139.88, 139.91, 141.37, 141.43, 141.57, 141.81, 141.98, 142.03, 142.06, 142.10, 142.12, 142.26, 142.30, 142.31, 142.41, 142.46, 142.50, 142.54, 142.97, 143.04, 144.37, 144.46, 144.61, 144.71, 144.98, 145.01, 145.03, 145.09, 145.20, 145.22, 145.26, 145.43, 145.65, 145.77, 145.81, 145.86, 145.91, 145.96, 145.97, 146.02, 146.10, 146.13, 146.25, 146.74, 146.83, 147.15, 147.25, 147.30, 154.98, 155.23, 156.25, 157.62, 160.01, 160.66

IR (KBr): ν (cm$^{-1}$)=2922, 2851, 2765, 1604, 1580, 1462, 1440, 1376, 1328, 1218, 1165, 1112, 810, 766, 722

UV/vis (hexane): λ (nm) (ε)=212 (150900), 255 (96200), 314 (33600)

MALDI-TOF-MS (HABA): m/z=1238.46 [MH]$^+$ (theoretical value of $C_{99}H_{60}NO_3^+$: 1238.46)

Elemental analysis (%): C, 90.40; H, 5.55; N, 1.17 (theoretical value of $C_{99}H_{60}NO_3$: C, 90.19; H, 4.80; N 1.13)

It was conformed from the above that the intended products Ex1 to Ex3 and Ex1' were obtained.

FIG. 1 is a view showing the observation result of the appearance of Ex1 to Ex3 by a digital camera.

FIGS. 1(A), (B) and (C) are the state of appearance of Ex1, Ex2 and Ex3, respectively. FIG. 1(A) shows that Ex1 has relatively high viscosity and is a wax state. FIG. 1(B) shows that Ex2 has low viscosity as compared with Ex1, but is an oil state. FIG. 1(C) shows that Ex3 has the lowest viscosity and is a liquid state. It was seen from those results that Ex1 to Ex3 obtained each are liquid at room temperature, although viscosity differs. Furthermore, it is suggested that the viscosity is decreased as the number of carbons in the alkyl substituent represented by the formula (1) is increased. Although not shown, it was confirmed that Ex1' is solid at room temperature.

Figure 2:
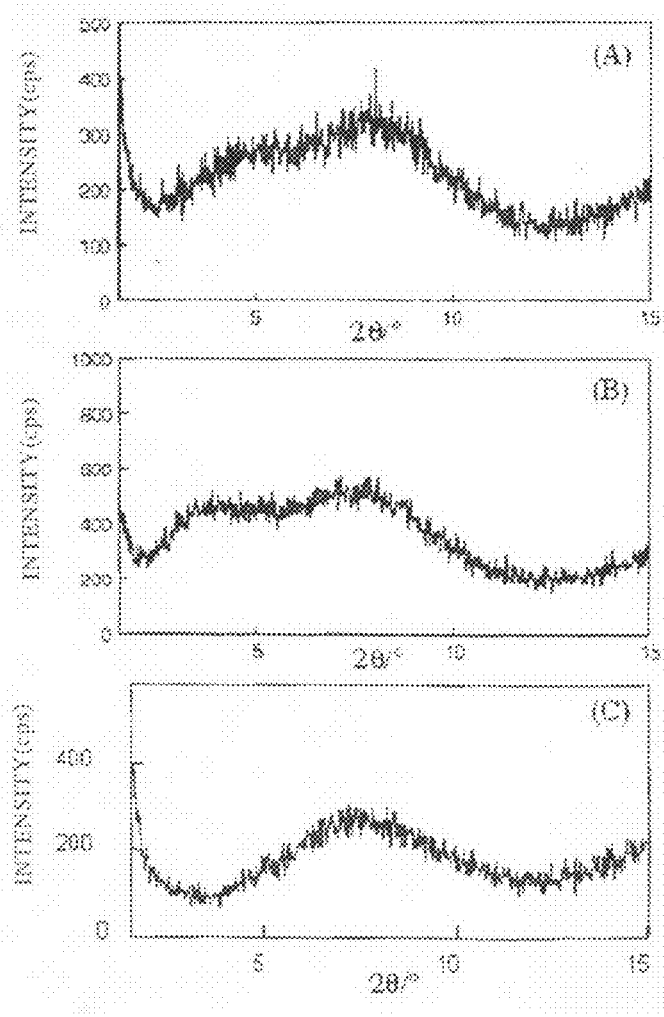
FIG. 2 is a view showing X-ray diffraction patterns of Ex1 to Ex3.

FIG. 2 is a view showing X-ray diffraction patterns of Ex1 to Ex3.

FIGS. 2(A), (B) and (C) are X-ray diffraction patterns of Ex1, Ex2 and Ex3, respectively. Ex1 and Ex2 show broad peaks at 2θ≈4.7° (d=1.9 nm) and 7.9° (d=1.1 nm), and 2θ≈3.8° (d=2.3 nm) and 7.5° (d=1.2 nm), respectively, and Ex3 shows broad peak at 2θ≈7.4° (d=1.2 nm), but did not show clear diffraction peak showing organized structure. Spacing d of the respective broad peak corresponds to the spacing of fullerene $C_{60}$ molecule. This fact suggests that fullerene derivatives of Ex1 to Ex3 do not have any regular cluster structure.

FIG. 3 is a view showing X-ray diffraction pattern of Ex1'.

The X-ray diffraction pattern of FIG. 3 shows clear plural diffraction peaks, and suggests that Ex1' has random tissue structure. In particular, the strongest diffraction peak was observed at 2θ≈5.5°. It was seen from this diffraction peak that the spacing d obtained is 1.6 nm and is comparable to the total length of octyl chain length and size of fullerene $C_{60}$ molecule. This fact suggests that the fullerene derivative of Ex1' has a tissue structure in the state that octyl chain is oriented.

FIG. 4 is a view showing frequency dependency of storage elastic modulus G" and loss elastic modulus G" of Ex1 to Ex3.

Storage elastic modulus G' and loss elastic modulus G" of Ex1 to Ex3 are satisfied with the relationship of G">G' over all of frequency. This fact indicates that Ex1 to Ex3 are all a fluidized state.

FIG. 5 is a view showing frequency dependency of viscosity of Ex1 to Ex3.

It was seen that viscosity is decreased in the order of Ex1, Ex2 and Ex3. It was seen from this result and the observation result of FIG. 1 that viscosity of the fullerene derivative obtained can be controlled by changing the number of carbon atoms in the alkyl substituent represented by the formula (1). Specifically, when it is desired to obtain a fullerene derivative having high viscosity, it is set such that the number of carbon atoms in the alkyl substituent represented by the formula (1) becomes small (close to 12), and when it is desired to obtain a fullerene derivative having low viscosity, it is set such that the number of carbon atoms in the alkyl substituent becomes large (for example, 20 or more).

The reason that viscosity is increased when the number of carbon atoms in the alkyl substituent is small (that is, length of the alkyl substituent is short) is considered to be due to that interaction between fullerenes becomes strong and cluster state is liable to be formed. On the other hand, the reason that viscosity is decreased when the number of carbon atoms in the alkyl substituent is large (that is, length of the alkyl substituent is large) is considered to be due to that π-π interaction between fullerenes is inhibited by the influence of the alkyl substituent and cluster state is difficult to be formed.

Figure 6:
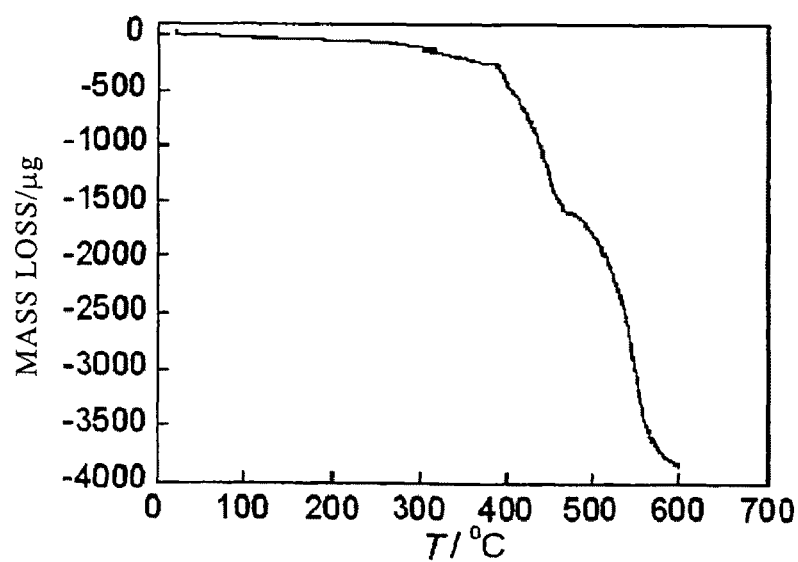
FIG. 6 is a view showing the result of thermogravimetric measurement of Ex3.

FIG. 6 is a view showing the result of thermogravimetric measurement of Ex3.

The thermogravimetric curve (TG curve) indicates that weight loss begins to cause at 395° C., and decomposition temperature of Ex3 is 395° C. Decomposition temperatures of Ex1, Ex2 and Ex1' similarly obtained were 340° C., 370° C. and 420° C., respectively. It was seen from this fact that any of fullerene derivatives are thermally stable.

Figure 7:
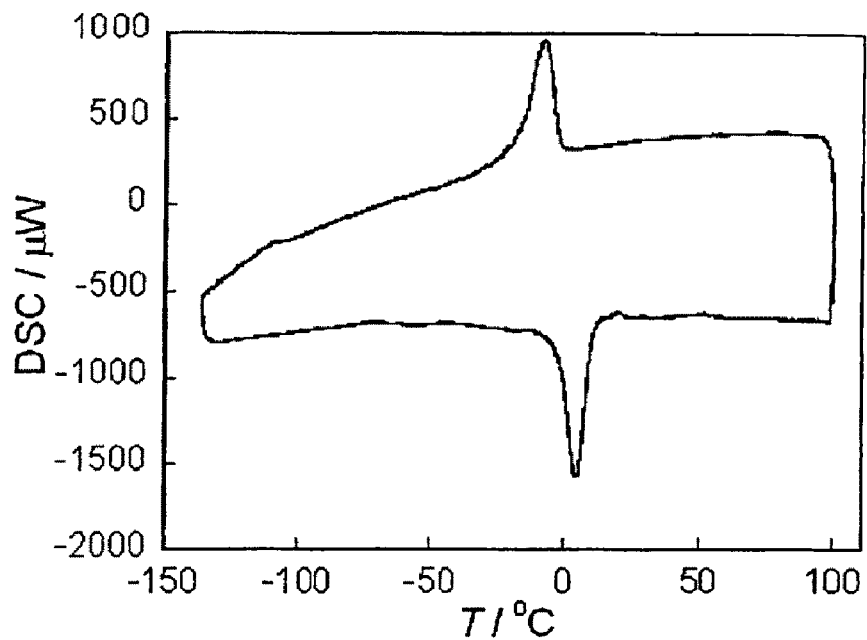
FIG. 7 is a view showing the result of differential calorimetry of Ex3.

FIG. 7 is a view showing the result of differential calorimetry of Ex3.

The differential calorimetric curve (DSC curve) showed an endothermic peak at 4° C. when heating and an exothermic peak at −8° C. when cooling. It was confirmed that the endothermic peak at 4° C. corresponds to a melting point, and the exothermic peak at −8° C. corresponds to a glass transition point. It was seen from FIG. 6 and FIG. 7 that Ex3 can maintain a liquid state from room temperature to 395° C.

DSC curves (not shown) of Ex1 and Ex2 did not show clear endothermic peak and exothermic peak. This is considered to be due to that change in heat quantity in Ex1 and Ex2 is so small, the change cannot be observed. DSC curve (not shown) of Ex1' showed an endothermic peak at 147 to 148° C. when heating.

The above results are shown in Table 1.

TABLE 1

| Sample | Decomposition temperature Td (° C.) | Melting point Mp (° C.) |
|---|---|---|
| Ex1 | 340 | — |
| Ex2 | 370 | — |
| Ex3 | 395 | 4.0 |
| Ex1' | 420 | 147-148 |

In the Table, the mark "—" indicates to be within measurement limit.

FIG. 8 is a view showing the result of cyclic voltammetry measurement of Ex1 to Ex3.

Each of the cyclic voltammetry curves (CV curves) showed clear oxidation-reduction reaction. It was seen that those CV curves each are the same as the CV curve of fullerene $C_{60}$. It was seen from this fact that even a solution having each of Ex1 to Ex3 dissolved therein maintains the property of fullerene $C_{60}$ without forming a cluster state.

FIG. 9 is a view showing the result of transient photocurrent measurement of Ex3.

FIG. 9 shows the result that transient photocurrent by formation of holes at applied voltages of 20V, 30V, 40V and 50V, and measurement time are logarithmically plotted. It was confirmed that transient photocurrent depending on the size of applied voltage flows. Travel time that the hole travels in the sample was obtained from folding points in the curve at applied voltages of 30V, 40V and 50V. The travel times at the applied voltages of 30V, 40V and 50V were 0.95 µs, 0.78 µs and 0.63 µs, respectively. As a result of calculating hole mobility using those travel times, distance between electrodes in the sample and applied voltage, it was found to be about 0.03 $cm^2/V$. This value is a relatively high value showing a liquid state, and is comparable to, for example, that of a polymer mixture of a methanofullerene derivative, and π-conjugated/organic conjugated oligomer which is a smetic liquid crystal phase. This fact suggests that the liquid fullerene derivative according to the present invention further has the function of a conjugated molecule, despite liquid.

Figure 10:
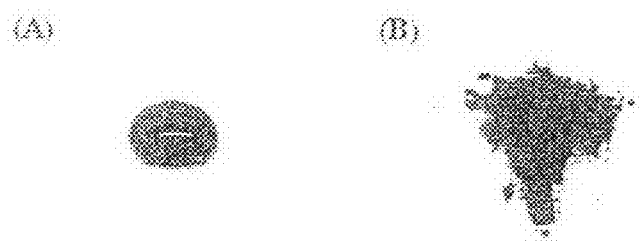
FIG. 10 is a view showing the observation result of appearance of Ex3 and Ex4 by a digital camera.

FIG. 10 is a view showing the observation result of appearance of Ex3 and Ex4 by a digital camera.

Ex3 was brown liquid as explained by referring to FIG. 1(C). On the other hand, Ex4 was brown solid. It was confirmed from the results (not shown) of $^1H$ NMR and calorimetric analysis that a residual solvent is not present in Ex4. Furthermore, it was confirmed that the result of identification of Ex4 is the same as that of Ex3.

Figure 11:
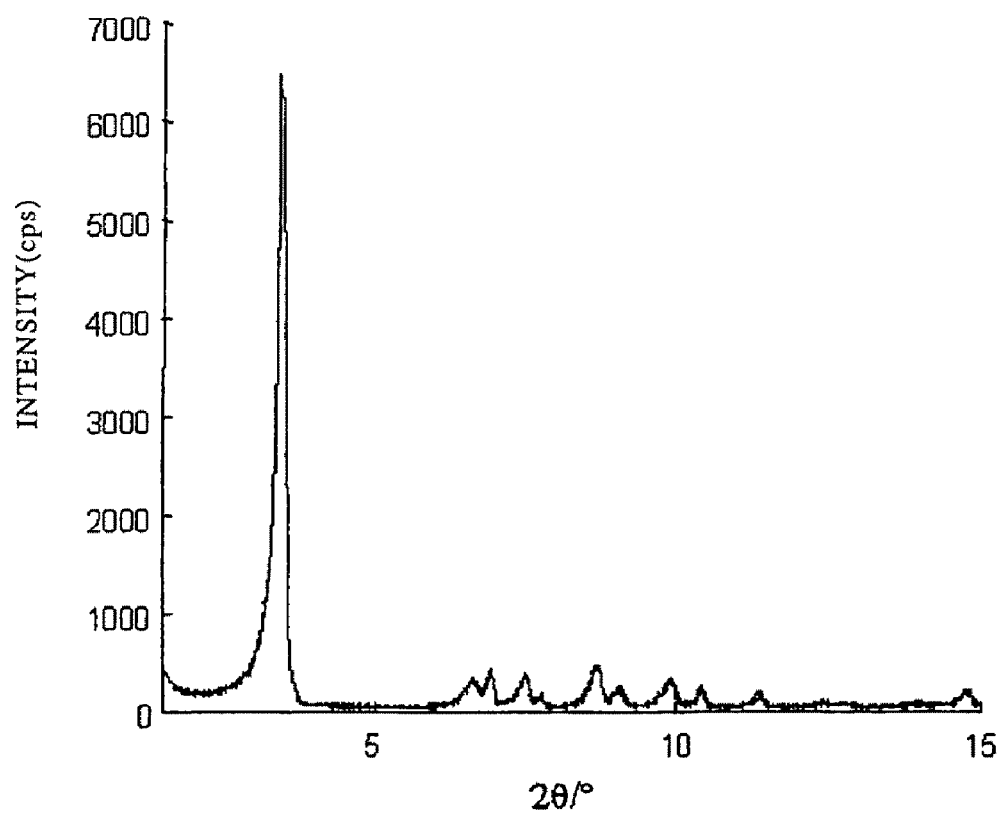
FIG. 11 is a view showing X-ray diffraction pattern of Ex4.

FIG. 11 is a view showing X-ray diffraction pattern of Ex4.

The X-ray diffraction pattern of Ex4 shows clear plural diffraction peaks, and suggests that Ex4 has a random aggregated structure. In particular, the strongest diffraction peak was observed at $2\theta=3.5°$. It was seen that this corresponds to the spacing d of 2.5 nm, and is similar to eicosyl chain length. This fact suggests that the fullerene derivative of Ex4 has an organized structure in the state that the eicosyl chain is oriented.

Figure 12:
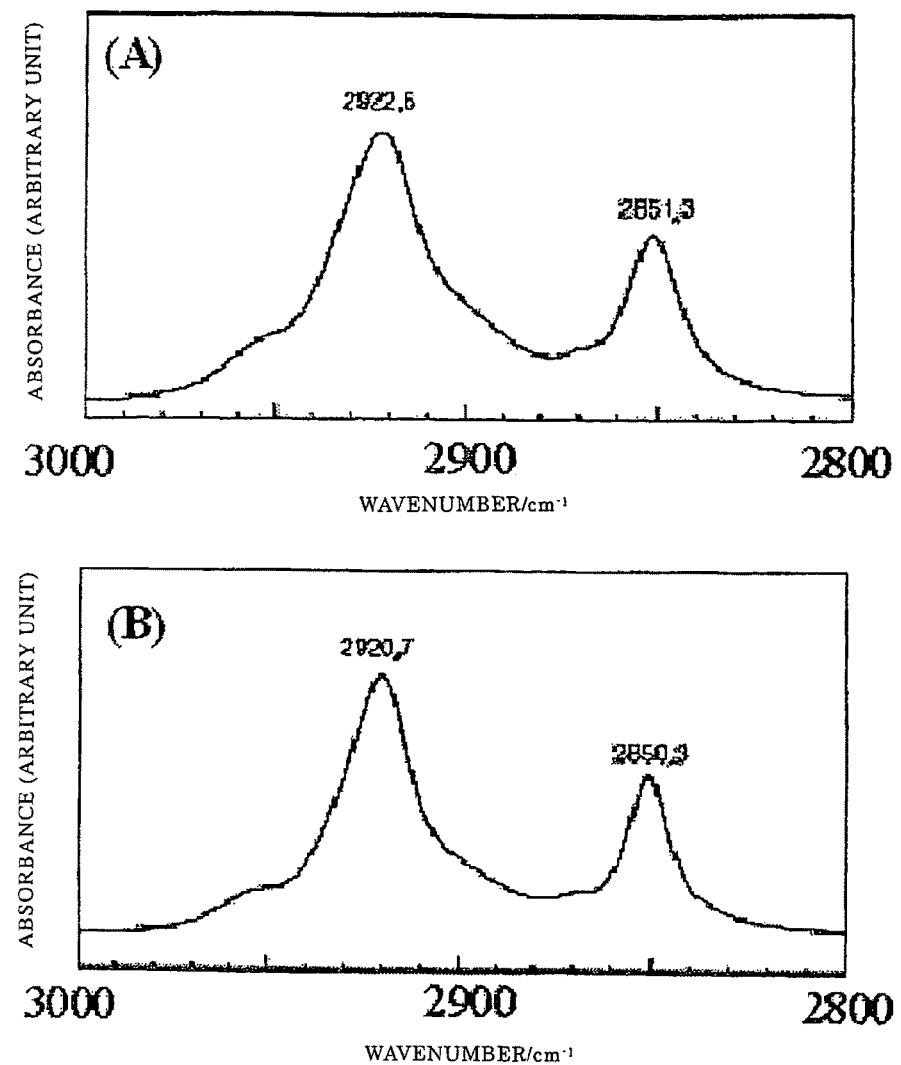
FIG. 12 is a view showing infrared absorption spectra of Ex3 and Ex4.

FIG. 12 is a view showing infrared absorption spectra of Ex3 and Ex4.

FIGS. 12(A) and (B) show infrared absorption spectra of Ex3 and Ex4, respectively. Peak by $CH_2$ expansion and contraction of the infrared absorption spectrum of Ex4 shifts to a low energy side (that is, high frequency side) as compared with that of Ex3. This fact suggests that the alkyl substituent of the fullerene derivative of Ex3 has a high crystallinity. It was seen from the results of FIG. 10 to FIG. 12 that the specific fullerene derivative according to the present invention can take different phase at room temperature by merely changing a solvent used.

Figure 13:
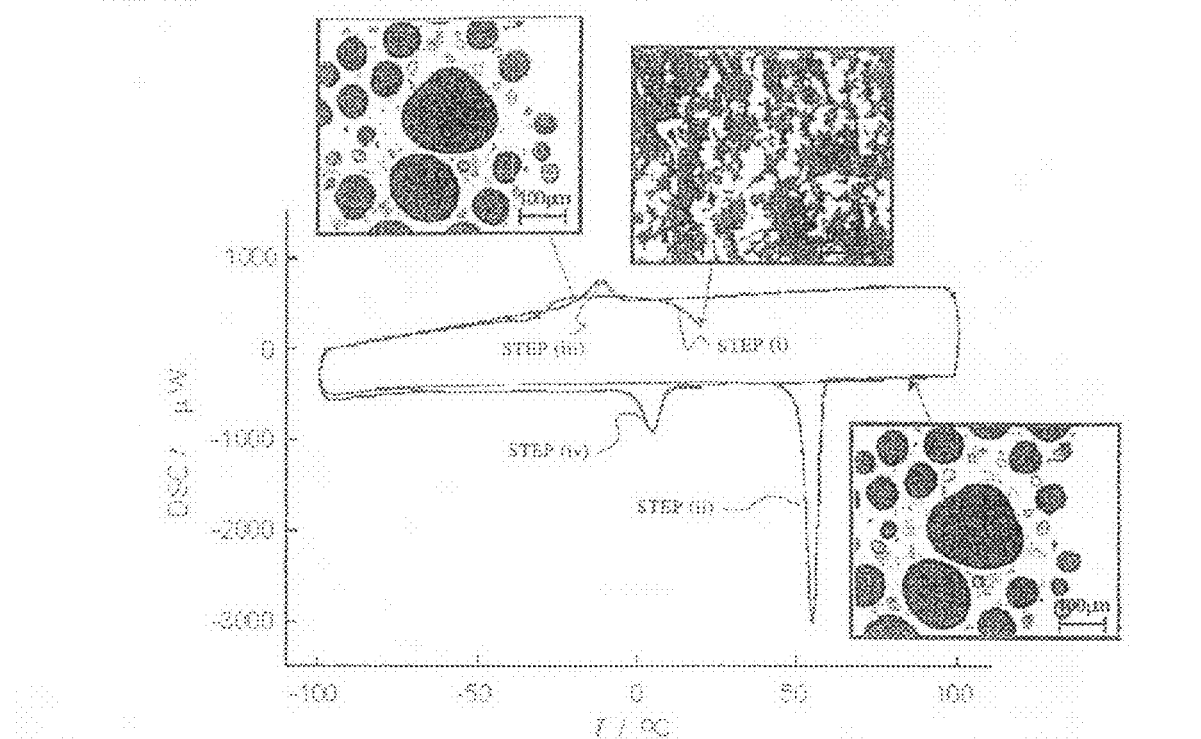
FIG. 13 is a view showing the result of differential calorimetry of Ex4.

FIG. 13 is a view showing the result of differential calorimetry of Ex4.

Step (i): cooling from 20° C. to −100° C., step (ii) heating from −100° C. to 100° C., step (iii) cooling from 100° C. to −100° C., step (iv) heating from −100° C. to 100° C., and repeating the cycle of step (iii) and step (iv). Change in heat quantity in each step was measured. FIG. 12 shows the result of change in heat quantity in one cycle of steps (i) and (ii) and steps (iii) and (iv), and the result of optical microscope observation of step (i) at a temperature of 20° C., step (ii) at a temperature of 80° C. and step (iii) at a temperature of −20° C.

The optical microscope observation of step (i) at a temperature of 20° C. shows a needle state showing crystal state at room temperature, and confirmed to be not liquid.

Clear change in heat quantity was not observed in step (i). Thereafter, clear endothermic peak was observed in the vicinity of 55° C. in step (ii). This endothermic peak was not observed in Ex3 explained in FIG. 7. The subsequent optical microscope observation of step (ii) at a temperature of 80° C. indicates isotropic liquid, and clear phase change of from solid to liquid was confirmed in Ex4. It was seen that 55° C. is a melting point of Ex. 4. Calculation of entropy at 55° C. indicates good consistency in the value of entropy of phase transition of an alkyl chain. It is considered from this fact that the interaction between the alkyl substituents of the fullerene derivative is enhanced at 55° C., thereby converting into liquid.

Exothermic peak was observed in the vicinity of −8° C. in step (iii). This consists with the behavior of Ex3 explained in FIG. 7 and corresponds to a glass transition point. As a result of optical microscope observation of step (iii) at a temperature of −20° C., it was confirmed that Ex4 maintains an isotropic liquid state even at a glass transition point or lower.

Endothermic peak was observed in the vicinity of 4° C. in step (iv). This consists with the behavior of Ex3 explained in FIG. 7 and corresponds to a melting point. Thereafter, endothermic peak was not observed in the vicinity of 55° C. in step (iv). Subsequently, as a result of repeating the cycle of step (iii) and step (iv), the same behavior as in FIG. 7 was observed (not shown).

It was seen from the above that Ex3 is in more stable state as compared with Ex4, and Ex4 formed from hexane as a volatile alkane is in a metastable state.

FIG. 14 is a view showing the result of cyclic voltammetry measurement of Ex3 and Ex4 applied to an electrode.

In FIG. 14, a solid line indicates the result of Ex3, and a dotted line indicates Ex4. Ex3 showed clear two-step oxidation-reduction reaction inherent in fullerene $C_{60}$ (the respective oxidation-reduction voltages were $E_{red2}=-0.74V$ and $E_{red2}=-1.02V$), similar to FIG. 8. On the other hand, Ex4 showed only one-step oxidation-reduction reaction (oxidation-reduction voltage was $-0.73V$ corresponding to $E_{red1}$ of Ex4).

Furthermore, Ex3 indicates change in quantity of electricity larger than Ex4, and giving and receiving of electron transfer is clearly confirmed. Ex4 is solid and is in a hard state. It is therefore considered that transfer of material is inhibited.

It was seen from this fact that Ex3 which is liquid can further exhibit the function of fullerene itself, as compared with Ex4 which is solid, and is therefore preferred.

INDUSTRIAL APPLICABILITY

The fullerene derivative according to the present invention is liquid at least at room temperature. Furthermore, the fullerene derivative according to the present invention is electrochemically active, has relatively high hole mobility, and can hold and exhibit the properties inherent in fullerene by itself. Such a fullerene derivative can be applied to, for example, a carbon electrode of a secondary battery and an electrochemical capacitor. Furthermore, the fullerene derivative can be used as a lead-free solder, a conductive paste or a conductive filler. The fullerene derivative according to the present invention can be applied to devices and materials that can use a fullerene.

The invention claimed is:

1. A liquid fullerene derivative represented by the following formula (1):

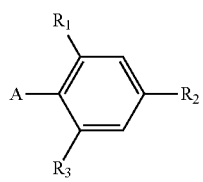

(1)

wherein $R_1$, $R_2$ and $R_3$ which are the same or different represent first to third alkyl substituents having at least 12 carbon atoms as the saturated alkyl chains; A represents a fullerene moiety represented by the following formula (2):

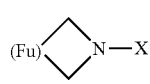

(2)

wherein (Fu) represents fullerene, X represents a methyl group; and a benzene ring is bonded to a nitrogen-containing five-membered ring of the fullerene moiety A, the first to third alkyl substituents $R_1$, $R_2$ and $R_3$ each being selected from the group consisting of alkyl ($C_nH_{2n+1}$), alkoxyl ($OC_nH_{2n+1}$) and thioalkyl ($SC_nH_{2n+1}$), wherein n is an integer of 12 or more.

2. The liquid fullerene derivative as claimed in claim 1, wherein the fullerene is selected from the group consisting of $C_{60}$, $C_{70}$, $C_{76}$, $C_{84}$ and endohedral metallofullerenes.

3. A method for producing a liquid fullerene derivative represented by the following formula (1):

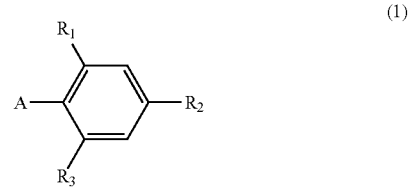

(1)

wherein $R_1$, $R_2$ and $R_3$ which are the same or different represent first to third alkyl substituents having at least 12 carbon atoms as the saturated alkyl chains; A represents a fullerene moiety represented by the following formula (2):

(2)

wherein (Fu) represents fullerene, X represents a methyl group; and a benzene ring is bonded to a nitrogen-containing five-membered ring of the fullerene moiety A, the first to third alkyl substituents $R_1$, $R_2$ and $R_3$ each being selected from the group consisting of allyl ($C_nH_{2n+1}$), alkoxyl ($OC_nH_{2n+1}$) and thioalkyl ($SC_nH_{2n+1}$), wherein n is an integer of 12 or more, which comprises a step of reacting benzaldehydes represented by the following formula (3)

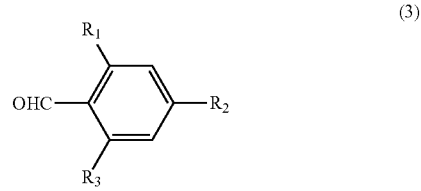

(3)

wherein $R_1$, $R_2$ and $R_3$ are the same as defined above, fullerene, and N-methylglycine.

4. The method as claimed in claim 3, wherein the fullerene is selected from the group consisting of $C_{60}$, $C_{70}$, $C_{76}$, $C_{84}$ and endohedral metallofullerenes.

5. The method as claimed in claim 3, wherein the reaction step is refluxed at 110° C. for 20 to 25 hours in dried toluene.

6. A conductive composition containing the liquid fullerene derivative as claimed in claim 1.

7. Electric and electronic devices comprising the liquid fullerene derivative as claimed in claim 1 as at least a part of its constitution.

8. A conductive composition containing the liquid fullerene derivative as claimed in claim 2.

9. Electric and electronic devices comprising the liquid fullerene derivative as claimed in claim 2 as at least a part of its constitution.

* * * * *